United States Patent [19]

Deblaere et al.

[11] 4,098,129
[45] Jul. 4, 1978

[54] NON-DESTRUCTIVE TESTING OF MATERIALS USING ULTRASONIC WAVES

[75] Inventors: Marie-Claude Deblaére, Paris; Alain Lambert, Creil; Christian Flambard, Gagny, all of France

[73] Assignee: Centre Technique des Industries Mecaniques, Senlis, France

[21] Appl. No.: 742,902

[22] Filed: Nov. 18, 1976

[30] Foreign Application Priority Data

Nov. 20, 1975 [FR] France .................... 75 35448

[51] Int. Cl.$^2$ ........................................... G01N 29/00
[52] U.S. Cl. ...................................... 73/599; 73/602; 73/624
[58] Field of Search ............. 73/67.7, 67.5 R, 67.8 R, 73/602, 599, 624

[56] References Cited

U.S. PATENT DOCUMENTS

| | | | |
|---|---|---|---|
| 3,572,099 | 3/1971 | Wieczorek | 73/67.7 |
| 3,776,026 | 12/1973 | Adler et al. | 73/67.7 |
| 3,937,067 | 2/1976 | Flambard et al. | 73/67.7 |

OTHER PUBLICATIONS

Rollins; "Critical Ultrasonic Reflectivity-Aneglected Tool for Material Evaluation," *Materials Evaluation*, Dec. 1966, pp. 683-689.

Parrett; "Reflection of Ultrasound at Liquid-Solid Interfaces," *Ultrasonics*, Jan. 1968, p. 9.

Fitch et al.; "Critical Angle Ultrasonic Tests," AEC Research and Development Report, 3-1964, pp. 1-5 and 8-11.

*Primary Examiner*—Richard C. Queisser
*Assistant Examiner*—Stephen A. Kreitman
*Attorney, Agent, or Firm*—McDougall, Hersh & Scott

[57] ABSTRACT

A method of non-destructively testing materials comprises directing an incident beam of ultrasonic waves onto the surface of a material and detecting the beam reflected by the surface, the angle of incidence and the wavelength of the ultrasonic waves being detected, and the critical angle of incidence at which the energy of the reflected beam passes through a minimum being determined for at least two different wavelengths. A curve is then prepared showing how the critical angle or a quantity dependent thereon varies with the wavelength or a quantity dependent thereon. Apparatus for carrying out the method comprises a goniometer for transmitting the incident ultrasonic beam and detecting the reflected beam, means for varying the angle of incidence of the beam, means for varying the wavelength of the waves, and means for determining the critical angles of incidence. The invention is applicable inter alia to the testing of tempered steel components.

12 Claims, 6 Drawing Figures

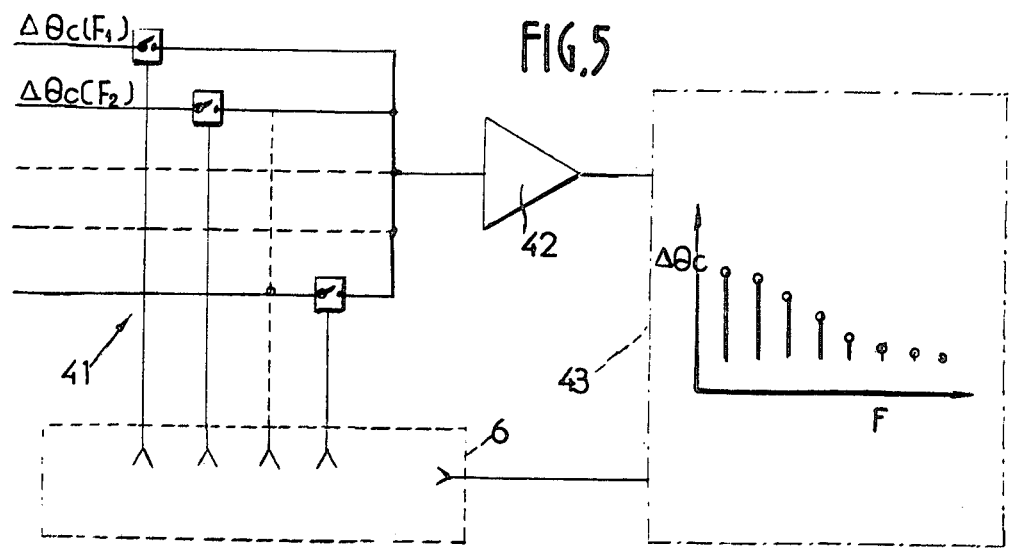
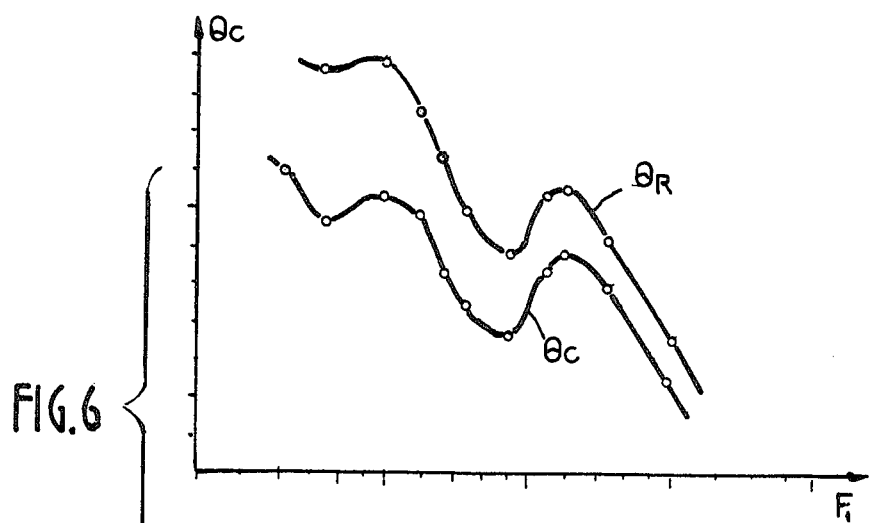
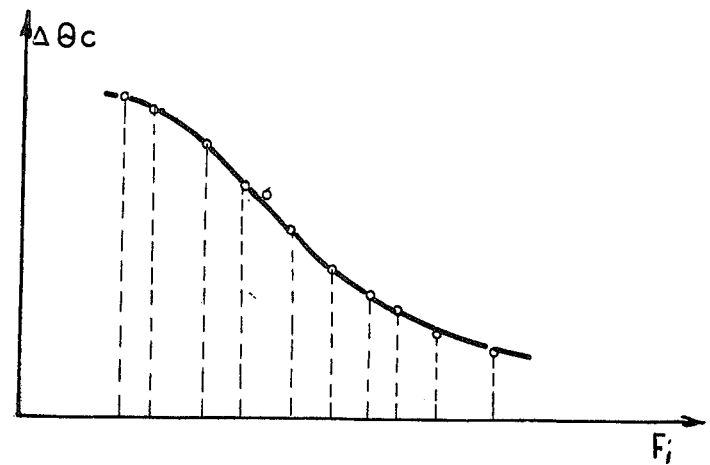

NON-DESTRUCTIVE TESTING OF MATERIALS USING ULTRASONIC WAVES

BACKGROUND OF THE INVENTION

This invention relates to the non-destructive testing of material using ultrasonic waves.

As is known, a study of beams of ultrasonic waves reflected from the surface of materials yields valuable information about mechanical properties of the surface layers of the materials, more particularly about the variations in Young's modulus, such as those which may be induced by thermal treatment of the material.

In this connection, there is a known method which comprises directing a beam of ultrasonic waves on to the surface of the material at a variable angle of incidence, detecting the energy of the corresponding reflected beam and determining the critical angle of incidence at which the energy (or the amplitude of the reflected waves) passes through a minimum. Rayleigh waves appear at the critical angle. The critical angle can be used, if required, to calculate the propagation speed of the Rayleigh ultrasonic waves at the surface of the material. This speed, and therefore the measured critical angle, depend on the surface hardness of the material. Allowing for the thickness of the surface layer involved in the propagation of the Rayleigh waves, the method can be used e.g. to estimate, by means of the thus-determined hardness, the depth at which a steel component has been tempered during cementation or other thermal treatment.

In spite of its importance, this method is limited in its applications since the hardness measured at each point on the surface of the material always corresponds to an average thickness of the material involved in the measurement, and cannot therefore be used for the testing of variations in hardness with depth.

SUMMARY OF THE INVENTION

The present invention concerns a method and apparatus for the non-destructive testing of materials by means of ultrasonic waves which, on the contrary, can be used to study variations in the mechanical characteristics with depth, starting from the surface of the material. The method and apparatus are applicable inter alia to the testing of tempered steel components, in which case it can be used to check the homogeneity of the tempered layer throughout its depth and to study variations in the structure and mechanical characteristics throughout the thickness of the layer and its neighbourhood.

According to the invention a method of non-destructively testing materials comprises: directing an incident beam of ultrasonic waves on to the surface of a material and detecting the beam reflected by the surface, the angle of incidence and the wavelength of the ultrasonic waves being detected; and determining the critical angle of incidence at which the energy of the reflected beam passes through a minimum for at least two different wavelengths.

The angle thus determined for each of the wavelengths used is the critical angle at which the Rayleigh waves appear. It is dependent on the propagation speed of the Rayleigh waves in a surface layer of the material having a thickness substantially equal to the corresponding wavelengths.

Advantageously, of course, the critical angles are thus determined at a given point on the surface of the material for a large number of progressively variable wavelengths. The results can be used to determine the propagation speed of the Rayleigh waves or the mechanical characteristics dependent on the last-mentioned speed, for progressively variable thicknesses of the material at the point in question, the thicknesses always being measured from the surface. If required, the thickness of the successive layers of material can be determined by differentiation.

Advantageously, the invention is applied to the examination of steel components which have been surface-tempered. Treatment of this kind is usually down to a depth of the same order as the wavelengths of ultrasound in the material, i.e. a few millimeters, whereas the resulting modifications in structure involve appreciable modifications in the Young's modulus and the speed of propagation of the Rayleigh waves. The method according to the invention can be used to examine variations in the depth of the tempered structure, whereas the prior-art ultrasonic methods of examination can be used only to evaluate the average depth of tempering.

In order to eliminate interfering variations in the measured critical angle or in the corresponding propagation speed, it is usually advantageous to compare, at each wavelength, the results obtained for the material under study (which is assumed to be non-homogeneous in depth at thicknesses of the same order as the wavelength) with the results obtained for a similar but homogeneous material. For example, the difference between the results for a tempered steel component and the results for a similar but non-tempered component is characteristic of the depth of tempering, and the variations in the difference with wavelengths can be used to represent variations in the thickness of the tempered structure with depth.

In a preferred embodiment of the method according to the invention, the incident beam is directed at different, progressively variable angles of incidence in succession; the waves of the reflected beam are detected at each value of the angle of incidence in the form of electric signals dependent on the amplitude of the waves in wave trains differing from one another by their frequency in a given frequency band; the signals are distributed in dependence on the frequency; the minimum amplitude is automatically determined for each frequency value; and the value of the corresponding angle of incidence is recorded.

In a method using analog electronic circuits to determine the energy minima, the signals can be distributed inter alia by allocating a different circuit to each frequency value. Alternatively, the signals can be processed in suitable digital computer programmed to calculate the amplitude minima. The different frequency values can be defined on transmission or on detection.

The invention also provides apparatus for non-destructively testing materials, comprising: a goniometer having means to direct an incident beam of ultrasonic waves on to the surface of a material and to detect the beam reflected by the surface; and means to vary the angle of incidence of the beam on the surface; means to vary the wavelength of the waves; and means to determine, for at least two different wavelengths, the critical angle of incidence at which the energy of the reflected beam passes through a minimum.

The measurements can be made by adopting different frequencies or wavelengths in succession and by making a complete angular scan of the beam at each frequency or wavelength so as to determine the corresponding critical angle. This method is, however, lengthy and the results are relatively inaccurate, since it is difficult to ensure successive identical angular scanning at different frequencies.

Preferably, therefore, the measurements are made during a single angular scan, the ultrasonic beam being frequency-scanned at each of the successive different values of the angle of incidence, after which the detected amplitudes are distributed in dependence on the frequency.

In the latter case, it is advantageous to use a particular embodiment of the apparatus according to the invention, comprising : automatic means for controlling and synchronizing a motor for step-by-step scanning of the angle of incidence; a generator for frequency scanning of the ultrasonic beam at each step; a receiver for receiving a detection signal having an amplitude proportional to the energy of the reflected beam and for distributing the amplitude values in dependence on the frequencies; and a processing unit which automatically determines the angle of incidence corresponding to the minimum energy for each frequency, starting from the aforementioned amplitude values and the successive values of the angle of incidence. The step-by-step scanning of the angle of incidence may be replaced by continuous slow scanning, which is then equivalent to step-by-step motion if the frequency scanning by the generator is rapid compared with the angular scanning.

In order to define the frequencies, use can be made of a generator producing successive wave trains different from one another in their frequencies in a given frequency band. Use can be made, for example, of a generator producing a single signal containing all the frequency information, associated with a receiver comprising frequency-controlled filters.

BRIEF DESCRIPTION OF THE DRAWINGS

In order that the invention may be readily understood, an embodiment thereof will now be described, by way of example, with reference to the accompanying drawings, in which :

FIG. 5 is a schematic diagram of a display device of the apparatus; and

FIG. 6 shows examples of curves obtained using the apparatus embodying the invention.

DESCRIPTION OF THE PREFERRED EMBODIMENT

Figure 1:
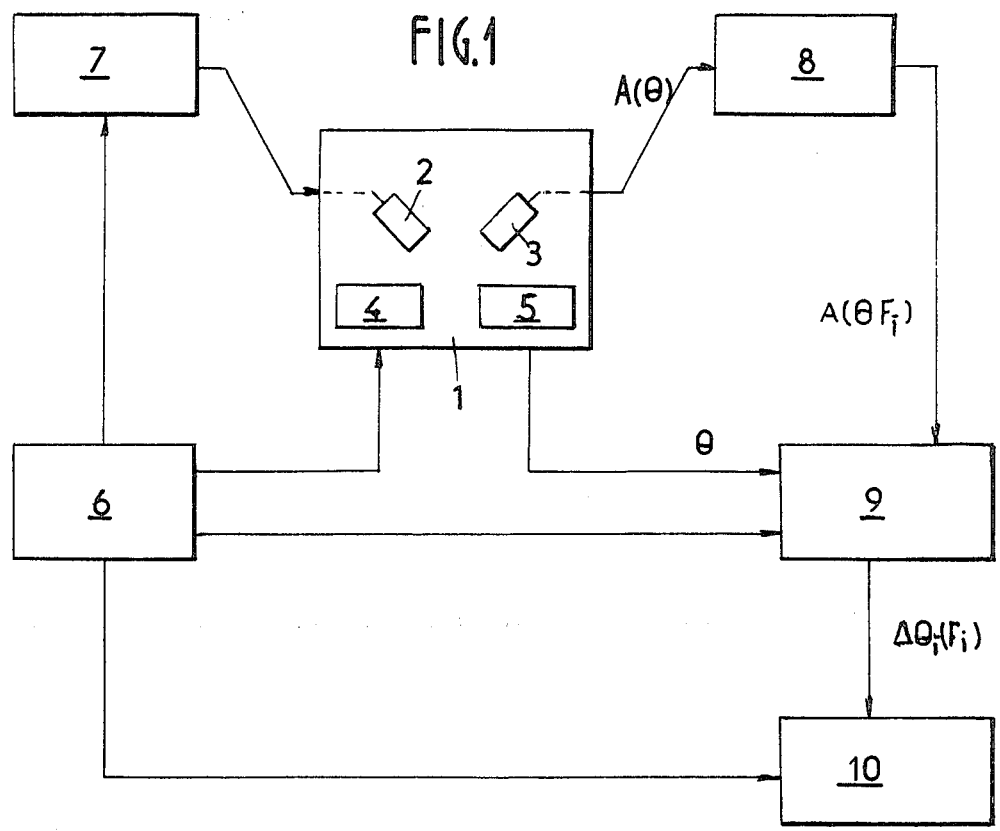
FIG. 1 is a general diagram of testing apparatus embodying the invention.

The apparatus represented by the general diagram of FIG. 1 can be used to direct an incident beam of ultrasonic waves on to the surface of a component (not shown) and to detect the beam reflected by the surface. The means used for this purpose comprise a goniometer of known type, e.g. such as described in French Patent Specification Nos. 70.20.302., 71.34.370 or 74.90.182.

Basically, goniometer 1 comprises two ultrasonic probes, i.e. a transmitting probe 2 and a receiving probe 3 permanently oriented so that probe 3 receives the beam reflected by the surface of the tested component when an incident beam is sent from probe 2 towards a fixed point on the component. The two probes can be combined in a single probe performing both functions alternately, if the goniometer is equipped with a cylindrical mirror for returning the beam in the opposite direction. Probe 3 comprises a detector supplying an electrical signal in dependence on the amplitude of the received ultrasonic waves.

Goniometer 1 is motor-driven. Motor 4 is an electric motor which, when actuated by an electric control signal, drives probe-shifting mechanisms as described in the aforementioned specifications, so as to vary the angle of incidence of the beam on the examined surface. A pick-up 5 sensitive to the position of the probes delivers an electric signal $\theta$ dependent on the value of the angle of incidence. The motor control signal is provided by an automatic central control system 6. It produces step-by-step scanning of the angle of incidence. System 6 also controls and synchronizes the different units forming the electronic assembly associated with the goniometer. These units comprise : an ultrasonic generator 7 which, at each angle of incidence, supplies one or more signals controlling the transmitting probe 2, thus ensuring frequency scanning of the ultrasonic beam; a receiver 8 which receives the signal having an amplitude proportional to the detected energy coming from probe 3 and distributes the information contained therein in dependence on the frequency; a processing unit 9 which determines the angle of incidence corresponding to the minimum reflected energy for each frequency, starting from the previously-mentioned information and the successive values of the angle of incidence $\theta$; and a device 10 for displaying the results.

Frequency scanning is carried out so as to cover a frequency range extending e.g. approximately from 1 to 10 MHz, this range being particularly suitable for a study of tempered steel components. The scanning can e.g. be by means of electric pulse having a wide power band and a short duration, e.g. pulses of a few hundred volts and from 50 to 100 nanoseconds, the duration being adjusted by switching a fast thyristor; in that case, each pulse is wide-band and contains all the frequency information, and the values of the frequencies considered for the different measurements are selected by frequency filters at the receiver 8. Alternatively, sinusoidal wave trains can be produced having a short duration (e.g. about 10 microseconds), the frequency of the wave trains changing slightly at each recurrence so as progressively to cover the entire frequency range used for the examination; the wave trains can be obtained by means of a programmable function generator followed by a wide-band power amplifier.

Figure 2:
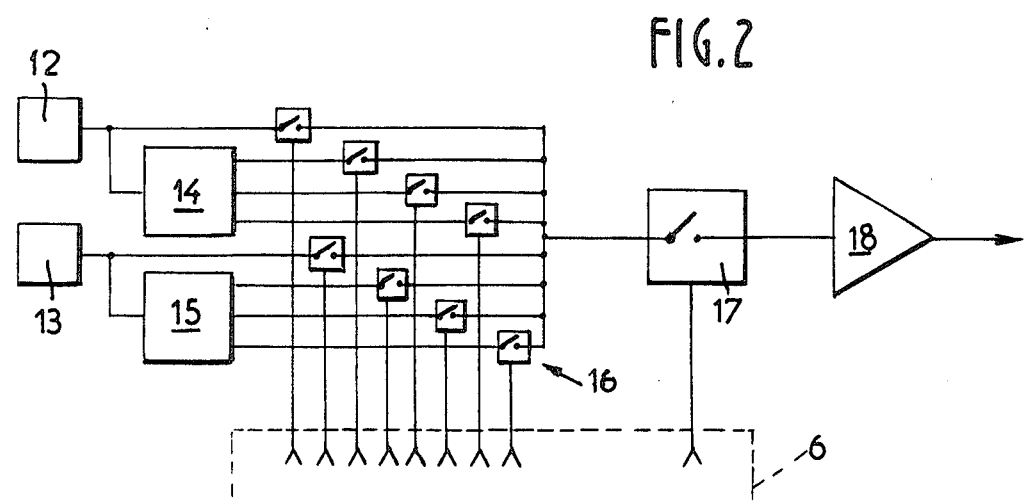
FIG. 2 is a synoptic diagram of an ultrasonic generator of the apparatus.

In the particular embodiment illustrated, the ultrasound generator 7, as shown in FIG. 2, is made up of a sequence of eight oscillators controlled by two crystals 12, 13 having frequencies 10 MHz and 7MHz respectively and frequency dividers 14, 15 adapted to generate sinusoidal frequencies at the following frequencies respectively :

10 MHz, 7 MHz, 5 MHz, 3.5 MHz, 2.5 MHz, 1.75 MHz, 1.25 MHz, 0.875 MHz.

A switch 16 controlled by the central system 6, can be used for obtaining the eight frequencies in succession, with a recurrence period of 500 microseconds. An analog gate 17, controlled by the central system 6, does not let the signals through except during a 10-microsecond period every 500 microseconds. The resulting signal is thus made up of eight successive wave trains lasting 10 microseconds. It is sent to the transmitting probe via a wide-band power amplifier 18. The complete cycles of eight frequencies follow at a recurrence rate of 5 ms.

The control of goniometer motor 4 is synchronized with the control of generator 7 so that a period of a few tens of microseconds is left between (a) each control pulse sent from system 6 to the motor and (b) the beginning of the frequency cycle, so that the motor has time to make an elementary rotation.

Receiver 8 is for distributing the receiving-probe amplitude signal among the different frequencies. It can be adapted to select frequencies itself, e.g. by means of an adjustable filter having a filtering frequency which is programmed so as to be slightly different at each recurrence, the amplitudes of the signals collected being stored for each frequency and each angle of incidence. Alternatively, filtering can be by means of a group of band-pass filters having slightly different central frequencies from one filter to another and arranged in parallel; in that case, the signals are separated into as many tracks as required.

Figure 3:
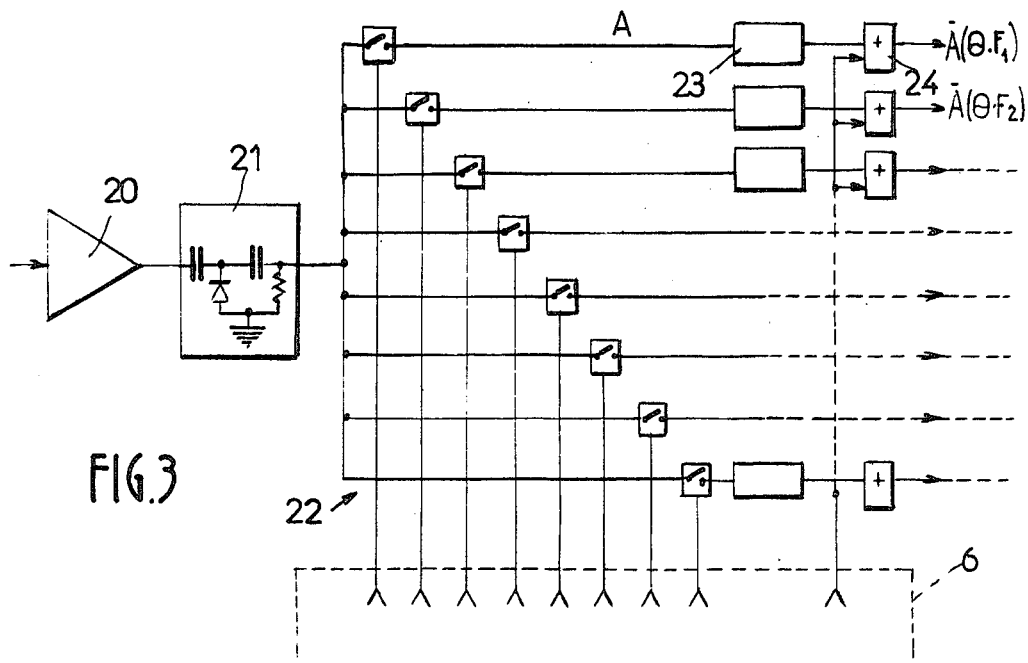
FIG. 3 is a schematic diagram of a receiver of the apparatus.

Advantageously, the generator in FIG. 2 is associated with a receiver shown synoptically in FIG. 3. At each scanning step of the angle of incidence, the signal of amplitude $A(\theta)$ representing the energy of the detected beam is amplified by a wide-band preamplifier 20, then rectified and filtered at 21 to obtain a signal containing only the envelopes of the negative half-waves of the wave-trains. A switch 22 actuated by the central system 6 distributes the different wave trains (which are clearly separated in time) among eight different tracks, respectively allocated to the different frequencies Fi. On each track, the amplitude of the received echo is measured at 23 and added to a positive d.c. voltage at 24 so as to invert the variation in the signal. Thus the amplitude, which varies in steps with the angle of incidence $\theta$, passing through a minimum corresponding to the critical angle of incidence, is converted into a voltage signal $\overline{A}(\theta, Fi)$ having a maximum.

Figure 4:
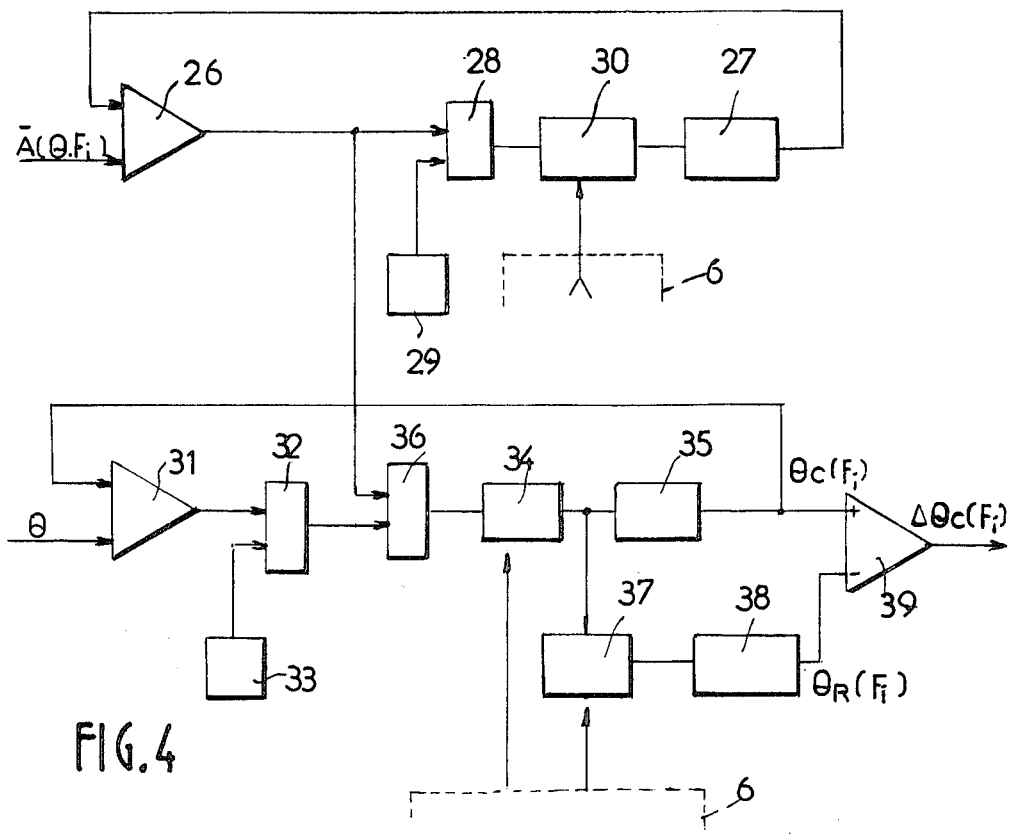
FIG. 4 is a schematic diagram of one of the identical circuits, each allocated to one frequency, in a processing unit of the appratus.

The critical angles are determined in the processing unit 9 by a completely analog electronic process. Unit 9 comprises eight circuits for detecting the maximum and determining the critical angle. The circuits are identical and only one of them is shown in the synoptic diagram in FIG. 4. The circuits respectively process the different signals $\overline{A}(\theta, Fi)$ corresponding to the different frequencies Fi and to complete scanning of the angle of incidence $\theta$.

In each circuit, the inverted amplitude $\overline{A}(\theta, Fi)$, is introduced at the input of a comparator 26, which compares it with the output voltage of a digital/analog converter 27. An AND circuit 28 passes pulses from a clock 29 as long as the voltage $\overline{A}(\theta, Fi)$ is greater than the converter output voltage, and the corresponding pulses are counted by a counter 30, the output of which is connected to the input of converter 27. At the same time, a signal proportional to the successive values of the angle of incidence $\theta$ and coming from pick-up 5 (FIG. 1) is processed in similar manner by a comparator 31, and AND gate 32, a clock 33, a counter 34 and a digital/analog converter 35. In addition, an AND gate 36 allows simultaneous counting on both circuits. Consequently, the counting stops when the voltage $\overline{A}(\theta, Fi)$ decreases after passing through a maximum, in which case counter 35 stores the value of the corresponding angle, i.e. the critical angle $\theta_c(Fi)$ corresponding to the frequency Fi considered in the circuit.

The value $\theta_c(Fi)$ can be stored at 37. Store 37 is used for recording the value of the critical angle obtained during a first series of measurement during the examination of a reference component. During a second stage, the component under study is compared with the reference component. A comparator 39 receives the output signal of converter 33, i.e. $\theta_c(Fi)$ and the output signal $\theta_R$ of a digital/analog converter 38 for converting the value stored at 37, and supplies a signal representing the difference $\Delta \theta_c(Fi)$. This operation is simultaneously performed in the different circuits associated with the different frequencies. As an alternative to the aforementioned analog method of detecting the energy minimum, a numerical method can be used, according to which the amplitude of the signal is converted into numerical form for each frequency and each angle, the amplitude value is compared with the corresponding value obtained at the same frequency as at the preceding angle, and the value is stored instead of the preceding value if it is lower than the preceding value.

FIG. 5 shows a display unit comprising a cathode ray tube 43 and a switch 41 which successively sends the different voltages proportional to $\Delta \theta_c(Fi)$ at the different frequencies to an amplifier 42 controlling plates for vertically deflecting the tube 43, whereas a stepped time base effects the horizontal scan, thus displaying a series of eight lines having an amplitude representing $\Delta \theta_c$, each line being characteristic of one frequency.

In the apparatus for FIG. 1, the entire aforementioned processing unit 9 can be replaced by a digital computer programmed to process the different values of $A(\theta, Fi)$. The results can be given directly as a variation in the propagation speed of the surface waves, calculated from the variations in the critical angles in accordance with the equation: $V = V_2/\sin \theta_c$, $V_2$ being the propagation speed of longitudinal waves in the coupling medium between the goniometer probes and the examined components.

FIG. 6 by way of example, shows the curves which can be obtained during testing of tempered steel components. The curve in the bottom part of the drawing represents the variations in the difference $\Delta \theta_c$ in dependence on the frequency F, the curve being based e.g. on the display on the cathode-ray tube. The curves in the top part represent the corresponding variations in the critical angle in the case (a) of the reference component ($\theta_R$) and (b) the component under study ($\theta_c$). The curve $\Delta \theta_c$ can be used to detect components having an unusual hardness gradient, (i.e. slight or considerable hardness of the tempered layer, decarburation, or very slow variation in hardness). Each frequency value determines the thickness of the surface layer taken into account in the corresponding measurements.

We claim:

1. A method for obtaining and displaying the variations of hardness of a hardened layer at the surface of a steel material comprising the steps of:

directing an incident beam of ultrasonic waves onto the surface of said material at varying angles of incidence and wave lengths of said waves;

detecting, for each of said wave lengths, the critical angle for the corresponding Rayleigh waves, said critical angle being equal to the angle of incidence at which the energy of the reflecting beam passes through a minimum and used to examine variations in the depth of the hardened structure;

displaying the variations of said critical angle as a function of frequency.

2. A method according to claim 1, comprising preparing a curve which shows how a quantity dependent on the critical angle varies in dependence on a quantity dependent on the wavelength.

3. A method according to claim 1, comprising preparing the results obtained, at thicknesses of the same order as the wavelengths, for a material having an inhomogeneous depth with the results for a similar but homogeneous material.

4. A method according to claim 1, comprising : directing the incident beam at different, progressively variable angles of incidence in succession; detecting the waves of the reflected beam at each value of the angle of incidence in the form of electric signals dependent on the amplitude of the waves in wave trains differing from one another by their frequency in a given frequency band; distributing the signals in dependence on frequency; determining the minimum amplitude automatically for each frequency value; and recording the value of the corresponding angle of incidence.

5. An apparatus for obtaining and displaying the variations of hardness of a hardened layer at the surface of a steel material comprising:
goniometer means for directing an incident beam of ultrasonic waves onto the surface of said material at varying angles of incidence and wave lengths of said waves;
means for detecting, for each of said wave lengths, the critical angle for the corresponding Rayleigh waves, said critical angle being equal to the angle of incidence at which the energy of the reflecting beam passes through a minimum and used to examine variations in the depth of the hardened structure;
means for displaying the variations of said critical angle as a function of frequency.

6. Apparatus according to claim 5, wherein the goniometer means delivers a detection signal having an amplitude proportional to the energy of the reflected beam, the apparatus comprising: a motor to drive the goniometer means; automatic means to control and synchronize the motor for step-by-step scanning of the angle of incidence; a generator to frequency scan the ultrasonic beam at each step of the angle of incidence; a receiver to receive the detection signal and to distribute the amplitude values in dependence on frequency; and a processing unit which automatically determines the critical angle of incidence for each frequency from the amplitude values and the successive values of the angle of incidence.

7. Apparatus according to claim 6, wherein the processing unit comprises a plurality of identical circuits each allocated to processing information relating to a given frequency.

8. Apparatus according to claim 6, in which the processing unit is a digital computer.

9. Apparatus according to claim 6, wherein the processing unit comprises means to store the values of the critical angles determined for the different frequencies during examination of a reference component and to determine, during examination of a component under test, the difference between the values for the reference component and the values measured for the test component at the same respective frequencies.

10. Apparatus according to claim 6, wherein the generator and the receiver comprises switching means synchronized so as respectively to transmit and distribute successive wave trains having frequencies slightly differing from one another for each angle-of-incidence scanning step.

11. Apparatus according to claim 6, wherein the generator is a wide-band pulse generator containing all the frequencies and the receiver comprises band-pass filters having central frequencies slightly different from one another and defining the said frequencies.

12. Apparatus according to claim 5, wherein the goniometer means delivers a detection signal having an amplitude proportioned to the energy of the reflected beam, the apparatus comprising: a motor to drive the goniometer means; automatic means to control and synchronize the motor for slow stepless scanning of the angle of incidence; a generator to frequency scan the ultrasonic beam rapidly compared with the scanning of the angle of incidence; a receiver to receive the detection signal and to distribute the amplitude values in dependence on frequency; and a processing unit which automatically determines the critical angle of incidence for each frequency from the amplitude values and the corresponding values of the angle of incidence.

* * * * *